United States Patent [19]

Leise, Jr.

[11] Patent Number: 5,004,464
[45] Date of Patent: Apr. 2, 1991

[54] CONVEX ADAPTER FOR OSTOMY DEVICE

[75] Inventor: Walter F. Leise, Jr., Yardley, Pa.

[73] Assignee: E.R. Squibb & Sons, Princeton, N.J.

[21] Appl. No.: 399,613

[22] Filed: Aug. 28, 1989

[51] Int. Cl.$^5$ .............................................. A61F 5/44
[52] U.S. Cl. .................................... 604/338; 604/344
[58] Field of Search ............... 604/277, 278, 332, 334, 604/337, 338, 339, 340, 341, 342, 343, 344

[56] References Cited

U.S. PATENT DOCUMENTS

| | | |
|---|---|---|
| D. 257,063 | 9/1980 | Galindo . |
| 3,302,647 | 2/1967 | Marsan . |
| 3,712,304 | 1/1973 | Marsan . |
| 3,805,789 | 4/1974 | Marsan . |
| 3,898,990 | 8/1975 | Nolan . |
| 4,213,458 | 7/1980 | Nolan et al. . |
| 4,219,023 | 8/1980 | Galindo . |
| 4,460,363 | 7/1984 | Steer et al. . |
| 4,710,182 | 12/1987 | Bryson . |
| 4,775,374 | 10/1988 | Cilento ............................ 604/338 |
| 4,834,731 | 5/1989 | Nowak et al. .................... 604/338 |
| 4,872,869 | 10/1989 | Johns ................................ 604/339 |

FOREIGN PATENT DOCUMENTS 0228191 8/1987 European Pat. Off. .

Primary Examiner—Randall L. Green
Assistant Examiner—Robert Clarke
Attorney, Agent, or Firm—James & Franklin

[57] ABSTRACT

For use with one piece and two piece ostomy devices, the adapter is situated on the adhesive-coated body side of the dressing which attaches to the skin surrounding the stoma to mount the collection pouch. The adapter includes a substantially rigid, annular member with a convex surface and an annular adhesive wafer. The wafer overlaps the edge of the member exposing a portion of the adhesive surface. The wafer and member are protected by a plastic shield. The wafer and member are applied to the body side of the dressing, with the convex surface of the member adjacent the wafer, as they are removed from the plastic shield. The exposed adhesive surface of the wafer directly contacts the adhesive of the body side of the dressing to form a secure bond. The result is a dressing with a convex shaped body side having a substantially uninterrupted layer of adhesive.

25 Claims, 5 Drawing Sheets

CONVEX ADAPTER FOR OSTOMY DEVICE

The present invention relates to ostomy appliances and more particularly to a convex adapter for use on the body side of one and two piece type ostomy devices.

Various types of surgical procedures, such as colostomies, ileostomies and urostomies, result in an opening or stoma in the abdominal area through which the body discharges waste. Since the patient has no control over the waste discharge, it is necessary to provide an appliance which both protects the stoma and acts as a collection receptacle for waste as it is discharged.

Many different types of ostomy devices are known in the art. The most popular devices include a planar flexible faceplate or dressing which has an adhesively coated side (body side) designed to be affixed to the skin of the patient surrounding the stoma. An opening in the faceplate aligns with and receives the stoma. A pouch or bag is sealingly attached to the reverse side (pouch side) of the faceplate, for example, by heat or impact welding, such that the inlet opening of the pouch aligns with the stoma receiving opening in the faceplate.

This form of an ostomy device is known as a "one piece" device because it consists of a single part, the pouch being permanently attached to the adhesive faceplate. With this type of device, when the bag is full, the entire device must be removed from the patient. Because the skin surrounding the stoma is often quite sensitive, it may be painful to remove the adhesive face-plate repeatedly. Accordingly, a system was devised in which the pouch is detachably mounted to the adhesive faceplate such that it can be removed and replaced when necessary, without requiring that the faceplate be removed. This is known as a "two piece" ostomy system.

U.S. Pat. No. 4,460,363, issued July 17, 1984 to Steer et al., and entitled OSTOMY BAG, disclosed a two piece ostomy device which has been very commercially successful. That patent teaches an ostomy bag which is securely coupled to the adhesive faceplate in a manner which will permit the bag to be removed without disturbing the faceplate. The system involves a first coupling member, in the form of a plastic ring which surrounds the stoma receiving opening in the faceplate, and a second coupling member, in the form of an annular channel, bonded to the ostomy bag around the inlet opening. The ring includes an upstanding rib or other projection which is dimensioned to sealingly engage an opening in the channel.

When the muscle surrounding the stoma of a patient lacks rigidity, because of advanced age or stretching, when the stoma does not sufficiently protrude beyond the skin surface or when the stoma has an adjacent depression, scar or crease, it has been found that the planar faceplates of conventional devices often do not adequately join with the peristomal skin to obtain the necessary fluid-tight and weight supporting seal. It has been discovered, however, that when the faceplate is provided with a convex curvature, a better seal between the peristomal skin and the faceplate results and a non-protruding stoma is also caused to protrude further into the stoma-receiving opening.

It is, of course, possible to fabricate ostomy devices with an adhesive faceplate having a convex curvature. However, it is impractical to produce a line of specialized ostomy devices in a variety of different sizes for use by the relatively limited number of patients who require this specialized configuration. Hence, a simple adapter has been used in conjunction with conventional ostomy appliances to produce faceplates with the required convex curvature.

Conventional adapters are designed for mounting on the pouch side of the faceplate, which is difficult on a one piece device where the pouch is permanently affixed to the pouch side of the faceplate.

However, one such system is shown in U.S. Pat. No. 4,219,023 to Galindo

Adapters designed for use with two piece devices are known. ConvaTec, a division of Squibb Corporation of Princeton, N.J., a leader in the area of ostomy products, has commercially successfully sold such a convex insert. This insert is designed specically for use only on two piece ostomy products. When properly affixed to the pouch side of the adhesive faceplate, the insert improves contact between the skin barrier and the peristomal skin area.

With the ConvaTec insert, the center hole in the faceplate is enlarged to fit the stoma prior to placing the insert into the coupling ring on the pouch side of the adhesive faceplate. The insert has an annular configuration with a convex surface and is made of substantially rigid plastic. Different size inserts are provided having different outer diameters which correspond to different size coupling rings.

While the ConvaTec insert does result in a faceplate having the necessary convex configuration, they may cause the pouch to accidentally detach from the faceplate. Such accidental detachments are a consequence which is very undesirable and often occur when the pouch is full due to the weight of the pouch. Because the convex insert is situated within the coupling ring on the pouch side of the dressing, it is between the pouch and the faceplate, and exerts an outwardly directed force on the pouch coupling ring which tends to detach same.

Recently, I have become aware of an ostomy appliance disclosed in U.S. Pat. No. 4,834,731 issued May 30, 1989 to Nowak et. al. which includes a convex pressure ring designed to be affixed to the body side of the faceplate to permit its use on both one and two piece devices. However, this structure has a severe disadvantage in that the adhesive of the convex ring does not directly contact the adhesive surface of the faceplate and thus a secure bond between the parts may not result. Moreover, the adhesive surface facing the patient is not uninterrupted.

It is, therefore, a prime object of the present invention to provide a convex adapter for use on one piece as well as two piece ostomy devices which securely bonds to the body side of an adhesive faceplate.

It is another object of the present invention to provide an annular convex adapter for an ostomy device which includes a larger diameter adhesive wafer with an exposed ring-like adhesive surface.

It is another object of the present invention to provide a convex adapter for an ostomy device in which the exposed adhesive surface of the adapter wafer bonds directly to the faceplate adhesive.

It is another object of the present invention to provide a convex adapter for an ostomy device which results in a faceplate with a substantially uninterrupted layer of adhesive on the body side.

It is another object of the present invention to provide a convex adapter for an ostomy device which is provided with a plastic shield formed to protect the adhesive wafer and prevent localized drying thereof.

In accordance with one aspect of the present invention, an adapter is provided for use with an ostomy device of the type including a faceplate having an adhesively coated body side for attaching a collection pouch to the body. The adapter comprises a substantially rigid member having a substantially convex surface and a layer of adhesive which overlaps the edge of the member. The member is situated between the adhesive layer and the faceplate with the convex surface adjacent the adhesive layer and the exposed portion of the adhesive layer contacting the adhesively coated body side of the faceplate.

The member preferably has a substantially annular configuration with a given outer diameter. The adhesive layer also preferably has a substantially annular configuration. The outer diameter of the adhesive layer is preferably larger than the outer diameter of the member, such that the adhesive layer overlaps the outer edge of the member to expose a portion of the adhesive layer which is substantially annular.

The member has a central opening of a given diameter. The adhesive layer also has a central opening. Preferably, the diameter of the central opening of the adhesive layer is smaller than the diameter of the central opening of the member, such that the adhesive layer overlaps the inner edge of the member as well, forming an annular exposed portion.

The adapter also includes a plastic shield for protecting the adhesive layer. The plastic shield has a contour substantially identical to the contour of the adhesive layer and the underlying member. The plastic shield has a substantially wrinkle-free surface.

In a two piece system, the faceplate may include connecting means for detachably mounting the pouch to the pouch side of the faceplate. The connecting means may be relatively rigid coupling rings having a given inner diameter. The outer diameter of the member is preferably smaller than the inner diameter of the coupling rings. The coupling rings define a circular area on the faceplate. It is with this area that the member is adapted to align.

In accordance with another aspect of the present invention, an adapter is provided for use with an ostomy device of the type including means having an adhesively coated body side for attaching a collection pouch to the body. The adapter comprises a substantially annular member with substantially convex surface and a substantially annular adhesive wafer. The adhesive wafer is larger in size than the member and overlaps the outer edge thereof to expose a portion of the wafer. The member is situated between the attaching means with the convex surface adjacent the wafer and the exposed wafer portion contacting the adhesively coated body side of the attaching means to form a body side with a convex contour and a substantially uninterrupted layer of adhesive.

Preferably, the diameter of the central opening in the member is larger than the central opening in the wafer such that the adhesive wafer overlaps the inner edge of the member as well.

To these and such other objects which may hereinafter appear, the present invention relates to a convex adapter for an ostomy device as described in detail in the following specification, taken together with the accompanying drawings, wherein like numerals refer to like parts and in which.

Figure 1:
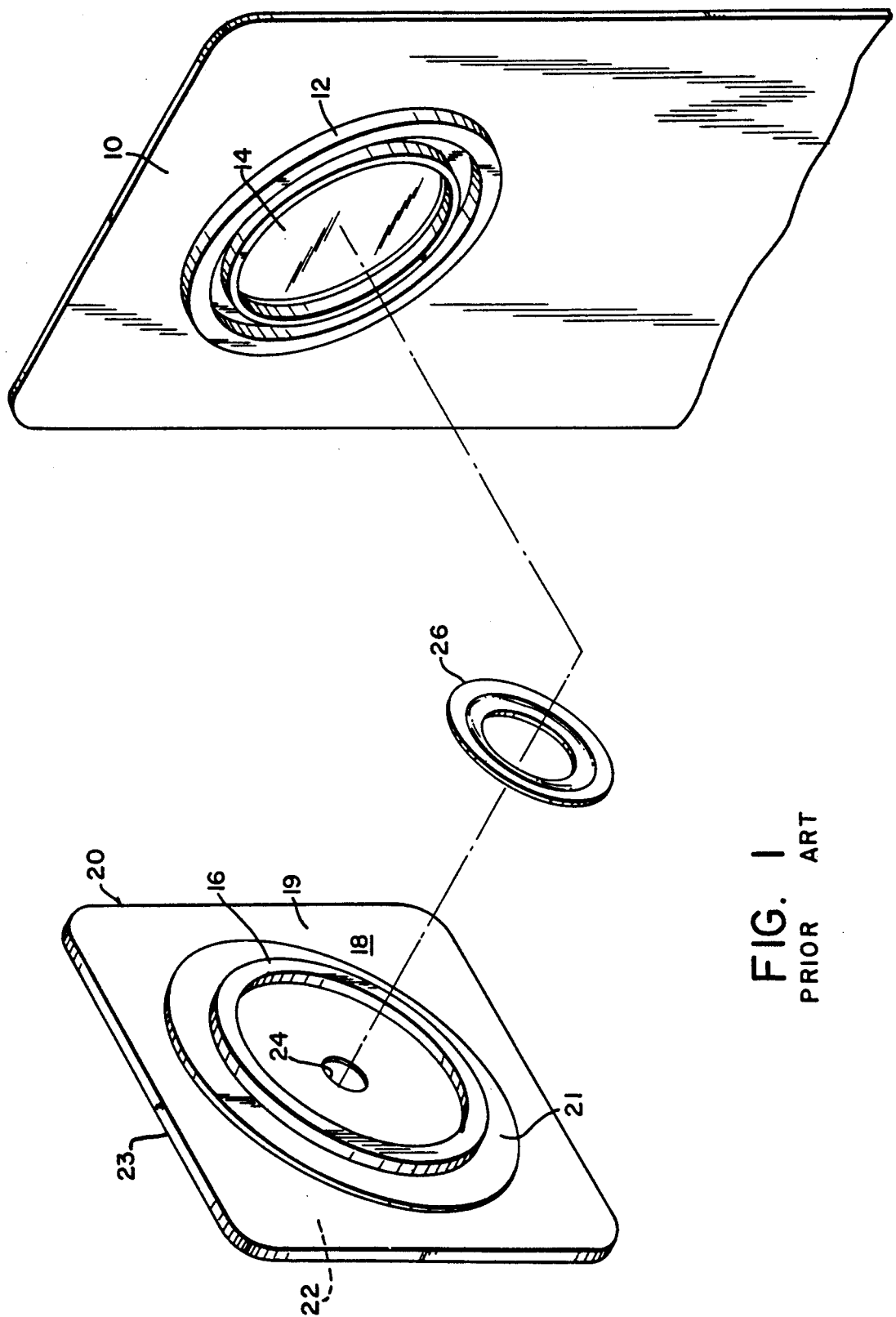
FIG. 1 is an exploded isometric view of a two piece ostomy device with a conventional convex insert.

FIG. 1 illustrates the Steer et al. two piece system described in U.S. Pat. No. 4,460,363 and a prior art convex insert designed for use therewith. The system includes an ostomy pouch 10 made of two sheets of thin, flexible film. The film is fabricated from materials which possess the properties of being moisture impermeable, odor impermeable and are capable of being heat sealed or impulse welded. Suitable materials include polyethylene, copolymers of polyethylene and ethylene vinyl acetate, copolymers of polyethylene acetate, copolymers of vinyl chloride and polyvinylidene chloride and laminates thereof. The pouch walls are preferably from about 2 to 4 mils thick. The walls are sealed around their periphery to provide a waste receptacle. The end of the pouch may be closed or open, as desired.

One wall of the pouch is provided with a coupling ring 12 in the form of a rigid plastic annular channel or groove which is welded or otherwise affixed to its exterior. The interior of ring 12 defines the stoma receiving opening 14 in the pouch.

Ring 12 is designed to be received over a second coupling ring 16 welded to the pouch side 18 of a flexible adhesive-backed faceplate 20. Coupling rings 12 and 16 sealingly inter-engage to demountably attach pouch 10 to faceplate 20. Faceplate 20 is covered by a thin film of polymeric material 19 to which the base 21 of coupling ring 16 is affixed. On the body side 22 of faceplate 20 is a layer of adhesive 23. The adhesive layer 23 can be any pressure-sensitive adhesive suitable for use on human skin and capable of supporting the weight of the appliance. Layer 23 of adhesive is covered by a sheet of release paper (not shown) prior to use.

In normal use, the opening 24 in faceplate 20 is designed to be custom fit to the stoma by the user. This is done by enlarging the opening until it fits snugly around the stoma. The faceplate is then affixed to the body of the patient such that the adhesive layer 23 of body side 22 adheres to the skin surrounding the stoma and the stoma protrudes through the enlarged opening 24. When the faceplate 20 is securely in place, bag 10 is mounted thereto by the appropriate mating of coupling rings 12 and 16.

In those instances where a convex configuration of the faceplate 20 is desirable, prior to mounting of the faceplate, a convex molded plastic insert 26 is pressed securely against the pouch side 18 of faceplate 20, within the area defined by coupling ring 16, preferably using the thumbs, while the faceplate is supported with the fingers. By pressing the insert securely into the faceplate, the configuration of the faceplate becomes convex, due to its flexibility.

It will will be readily appreciated that in the prior art system, the convex insert is installed on the pouch side of the adhesive faceplate and hence interposed between the faceplate and the pouch, in the area defined by the coupling rings. This being the case, the insert may tend to cause accidental decoupling of the rings, particularly when the pouch is weighted due to waste. As described in detail below, this disadvantage of the prior art insert is totally eliminated by the present invention.

FIGS. 2 through 5 illustrate the present invention. The present invention is illustrated as it would be used on a conventional two piece ostomy device, similar to that disclosed in the aforementioned Steer patent. However, the adapter of the present invention is suitable for use, in the identical manner, on one piece ostomy devices as well. It is designed to be affixed to the body side of the faceplate. Since the body side of the adhesive faceplate is essentially the same whether the device is a one piece device or a two piece device, the adapter of the present invention can be secured to either type appliance with equally good result.

Figure 2:
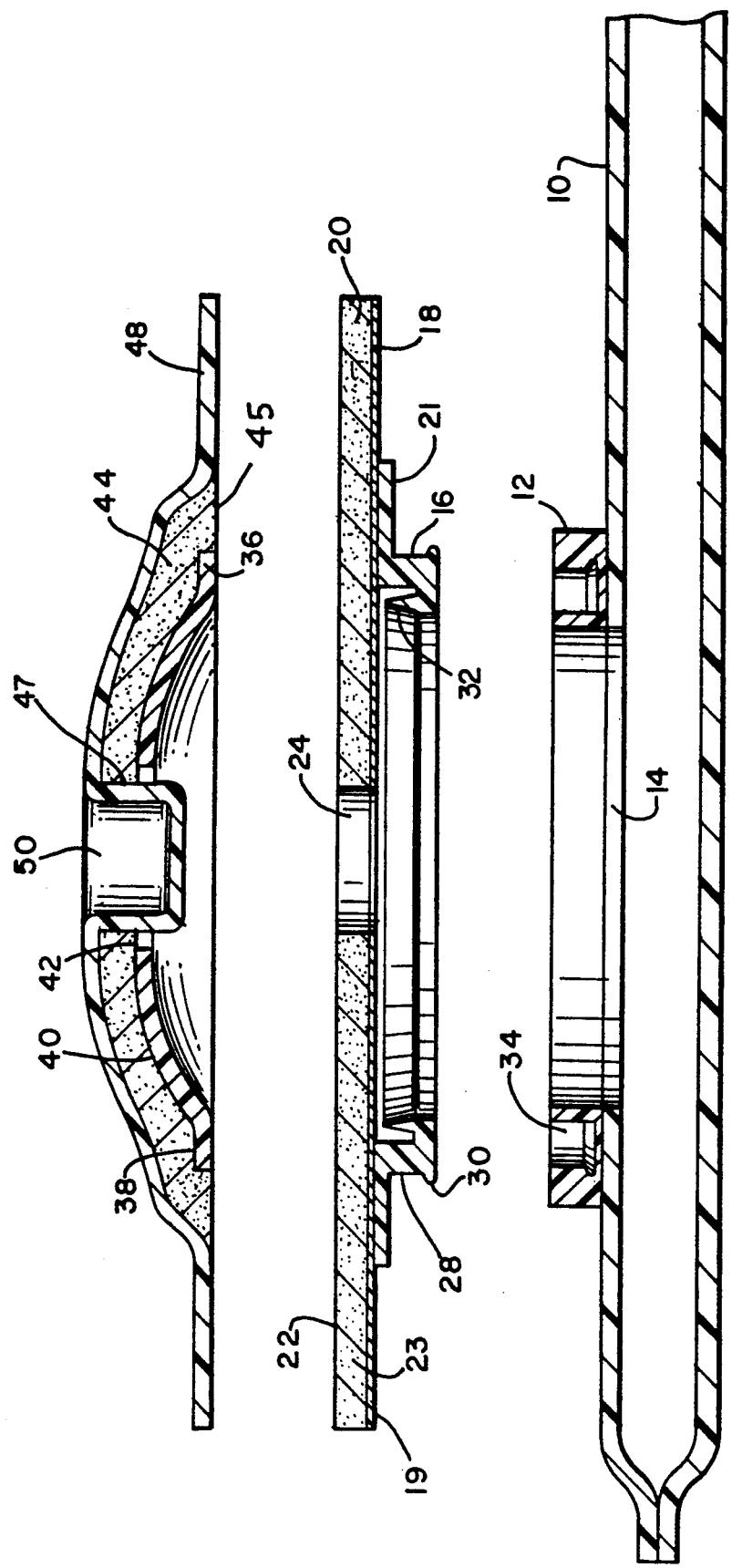
FIG. 2 is a cross-sectional view of a two piece ostomy device and the adapter of the present invention prior to the mounting thereof.
Figure 3:
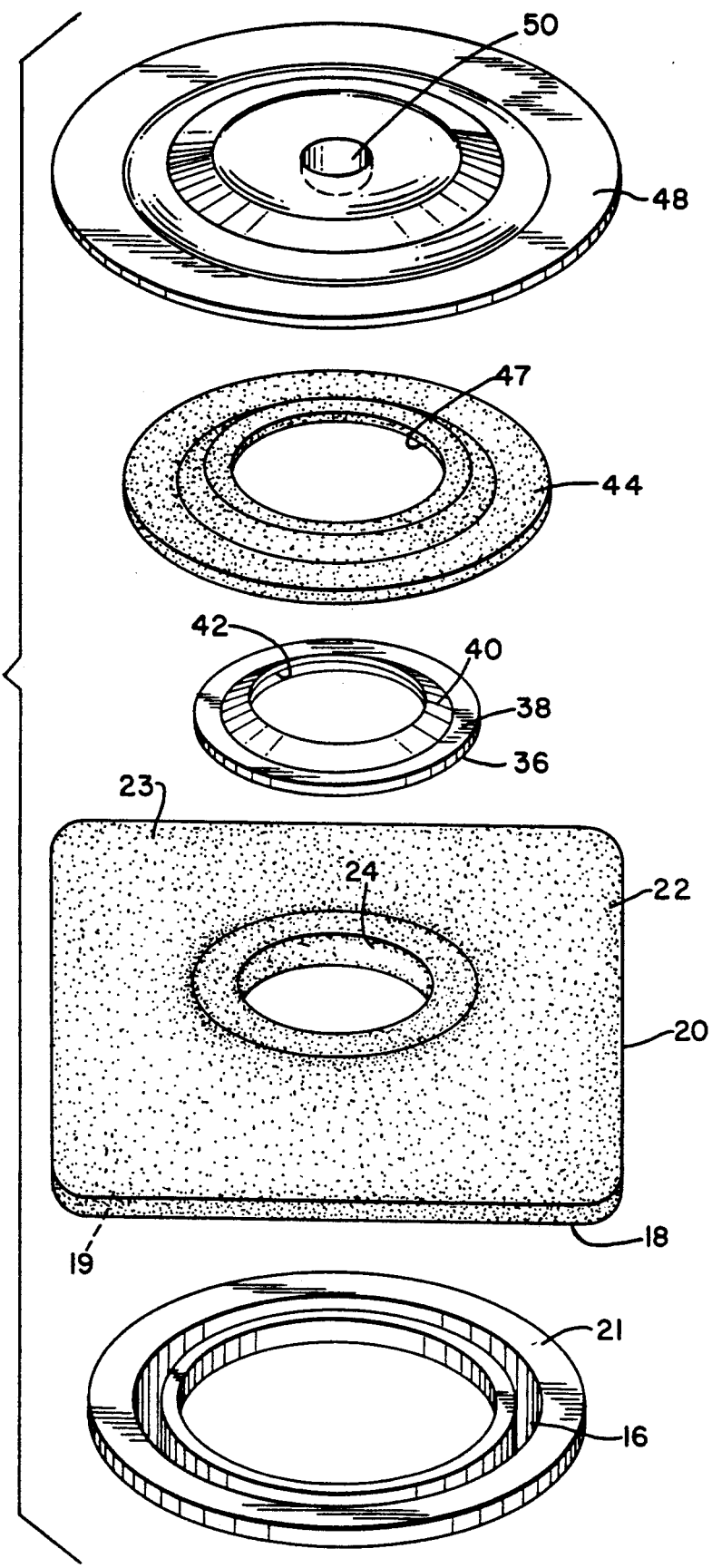
FIG. 3, is an exploded isometric view of the adapter of the present invention and the adhesive dressing of a two piece ostomy device.
Figure 4:
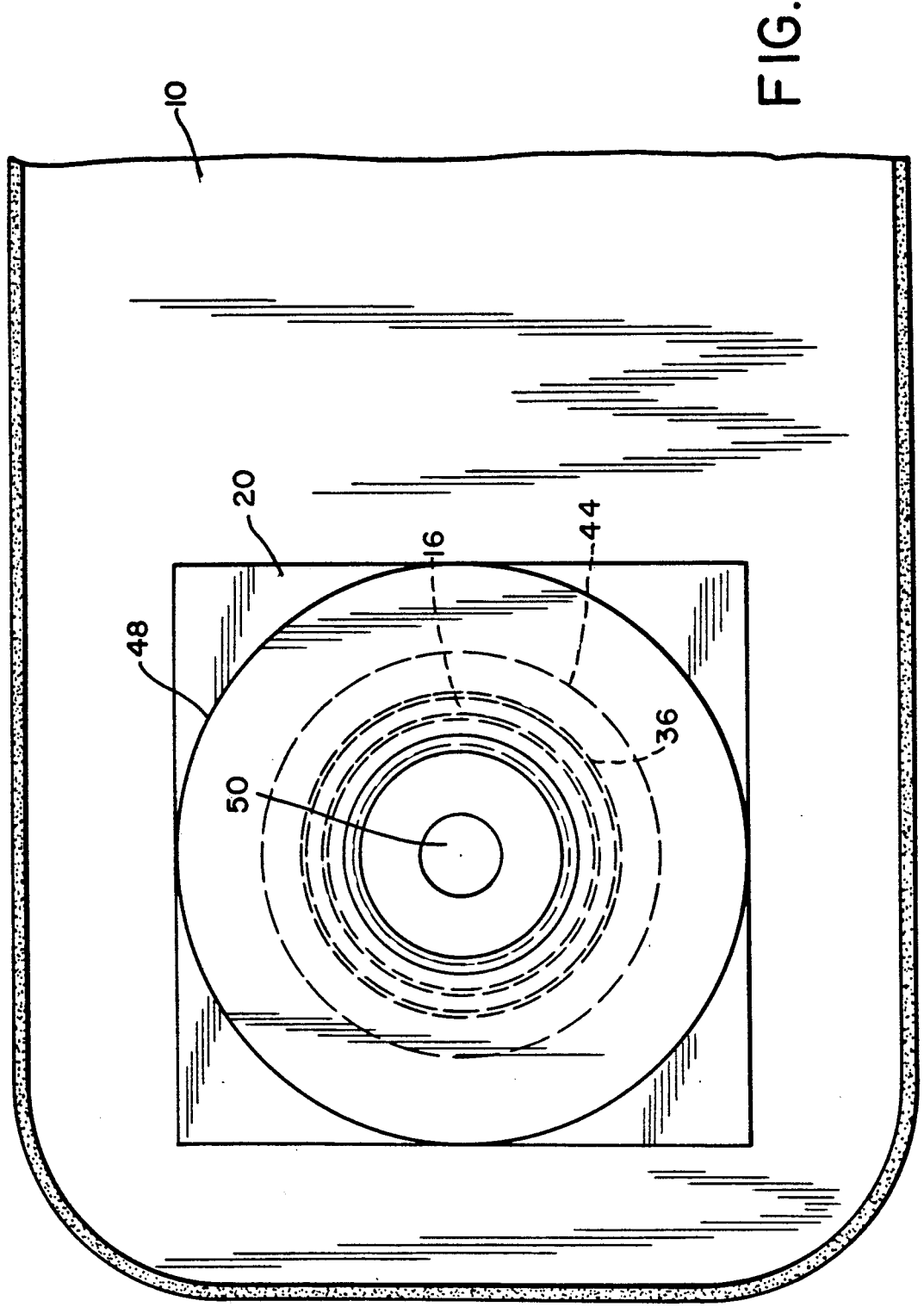
FIG. 4 is a plan view of the adapter of the present invention mounted on a two piece ostomy device.
Figure 5:
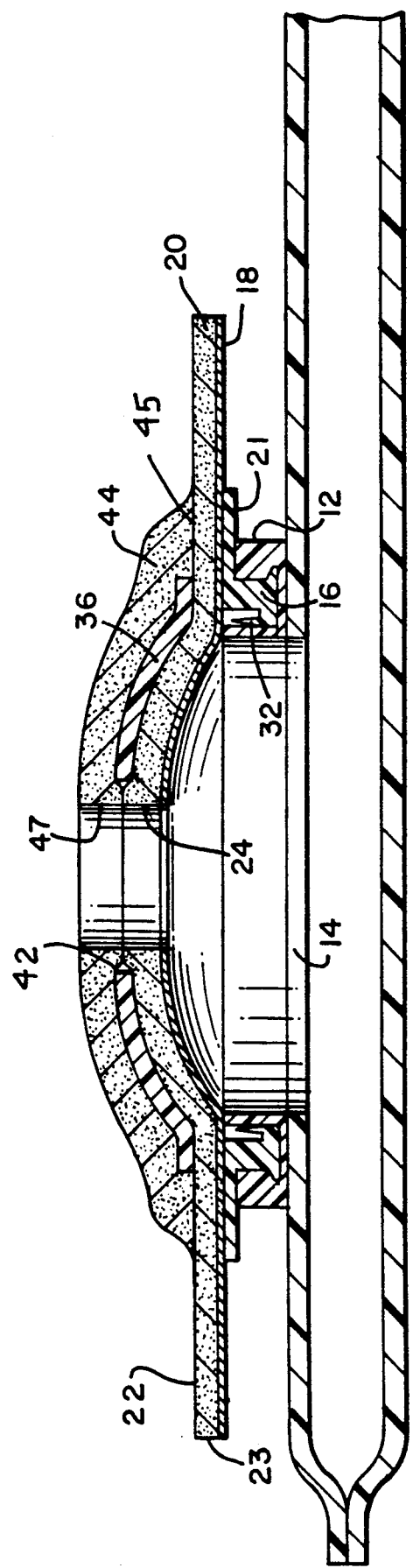
FIG. 5 is a cross-sectional view of the adapter of the present invention mounted on a two piece ostomy device, with the plastic shield removed and stoma receiving openings enlarged.

As mentioned above, the conventional adhesive backed faceplate 20 has a pouch side 18 to which coupling ring 16 is affixed. The ring may be affixed by welding or the like the undersurface of base 21 of ring 16 to the film surface 19 of the pouch side 18 of faceplate 20. As best seen in FIGS. 2 and 5, coupling ring 16 includes an upstanding annular wall 28 with projections 30 and 32 designed to sealingly mate with channel 34 of the coupling ring 12, which is affixed to the exterior surface of the wall of pouch 10. It should be appreciated that the particular configuration of the coupling rings forms no part of the present invention and should not be considered a limitation thereto.

The adapter of the present invention includes a rigid or semi-rigid (sufficiently rigid to maintain its shape under normal use conditions) annular member 36 which has a surface with a substantially planar peripheral portion 38 and a substantially convex central portion 40. Portion 40 has a central opening 42. Member 36 can be fabricated of plastic, such as by injection molding or the like, or can be formed of any other suitable material of sufficient rigidity.

Situated adjacent the upper surface of member 36 is an adhesive wafer 44, with a central opening 47. Adhesive wafer 44 can be formed of any pressure-sensitive adhesive suitable for use on human skin and capable of supporting the weight of the ostomy appliance. Preferably the adhesive consists of an elastomeric substance such as polyisobutylene containing one or more hydrocolloids, as taught by Chen in U.S. Pat. No. 3,339,546, by Chen et al. in U.S. Pat. No. 4,192,785, by Pawelchak in U.S. Pat. No. 4,393,080, or it can additionally include a styrene type block copolymer as taught by Doyle et al. in U.S. Pat. No. 4,551,490. The adhesive wafer preferably will be from about 20 to 70 mils thick.

Wafer 44 preferably has a substantially annular configuration with an outer diameter larger than the outer edge of member 36 such that it overlaps the outer edge of member 36 to expose an annular portion 45 of its surface. In addition, the diameter of central opening 47 of wafer 44 is preferably smaller than the diameter opening 42 of member 36 exposing an annular portion 60 adjacent opening 47. Thus, wafer 44 preferably overlaps the inner and outer edges of member 36.

As best seen in FIG. 5, portion 45 of the undersurface of wafer 44 contacts and adheres directly to the adhesive layer 23 body side 22 of faceplate 20. Further, the exposed portion of wafer 44 along the opening 47 contacts and adheres directly to adhesive layer 23. It should be noted that the inner rim of the adhesive tends to flow around the inner edge of member 36 as the parts are squeezed together.

Direct contact between the adhesive wafer 44 and the adhesive of the body side of faceplate 20 is important if a secure bond between the two is to be achieved. This feature is entirely lacking in the device disclosed in U.S. Pat. No. 4,834,731, discussed previously. It is preferably but not necessary that the contact be along the inner rim of the wafer as well as along the outer edge.

The exposed upper surface of wafer 44 is covered and protected by a plastic shield 48, which is vacuum formed over the wafer by a process which causes the plastic shield to have a configuration which is substantially identical to the contour of wafer 44. In spite of the fact that the plastic shield is formed from a planar sheet of plastic material, the vacuum forming process permits it to assume the precise convex shape of the upper surface of wafer 44 without wrinkling and without permitting air pockets between it and wafer 44, which would result in localized drying of the adhesive.

Although it forms no part of the present invention, the aforementioned vacuum forming fabrication method is described in detail in copending Application Ser. No. 399,829, entitled OSTOMY DEVICE WITH CONVEX ADHESIVE FACEPLATE AND PROTECTIVE SHIELD AND METHOD FOR FABRICATING SAME and the reader is referred to that application for the details thereof.

As best seen in FIG. 2, adhesive faceplate 20 is substantially planar before the adapter of the present invention is mounted thereon. The adapter includes convex member 36 and adhesive wafer 44 which are covered by plastic shield 48. The underside of the adapter may be covered with release paper if desired to protect the exposed adhesive surface portions. The release paper is removed prior to mounting.

Before affixing the adapter, opening 24 in faceplate 20 is enlarged to the desired size. Then an adapter of the appropriate size is chosen. In order to assist in choosing the appropriate size adapter, the protective shield 48 on the adapter is provided with an indentation 50 designed to fit into opening 24. Different size adapters have shields with different size indentations. The indentation 50 also acts as a guide and assists in centering the adapter on the dressing. Thus, the adapter may be aligned with the body side 22 of the adhesive backed faceplate 20 by aligning indentation 50 of shield 48 with the stoma receiving opening 24.

From the pouch side of faceplate 20, the thumbs are used to press the portion of the faceplate adjacent aperture 24 such that it conforms to the concave undersurface of member 36, as seen in FIG. 5. As this is done, the adhesive in wafer 44 is squeezed such that it flows toward the surface of faceplate 20 along the rim of opening 24 and along the outer edge of member 36 and is in direct contact with the adhesive of the faceplate. Thereafter, plastic shield 48 (which is preferably provided with a release agent) is removed by peeling same away from the faceplate and the faceplate may now be affixed to the body of the patient. Once the faceplate 20 is adhesively affixed to the body, pouch 10 can be coupled thereto in a conventional fashion, as illustrated by FIG. 5.

The above illustrations of the present invention depict same as it would be used on the Squibb SUR-FIT two piece system, as described in the above-noted Steer patent. SUR-FIT is a registered trademark of E.R. Squibb & Sons, Inc. However, it my be employed in the Squibb SUR-FIT FLEXIBLE SYSTEM, which includes a faceplate with an extended integral picture frame type with thinner adhesive and hence more flexibility, as described in U.S. Pat. No. 4,775,374, issued Oct. 4, 1988 to Cilento et al., with equally good results.

As will now be readily appreciated, body side 22 of faceplate 20 and adhesive wafer 44 form a substantially uninterrupted layer of adhesive, suitable for making a fluid-tight seal with the peristomal skin. Since adhesive wafer 44 has substantially the same convex contour as member 36, the faceplate and adapter combination is similar in all respects to a faceplate which has been manufactured with an internal convex member and a uniform body side adhesive coating. However, the adapter of the present invention eliminates the necessity of fabricating specialized convex faceplates as it can be used to adapt any conventional planar faceplate to have a convex configuration. Moreover, it can be mounted on both one piece and two piece devices in an extremely secure manner.

While only a single preferred embodiment of the present invention has been disclosed for purposes of illustration, it is obvious that many modifications and variations could be made thereto. It is intended to cover all of these modifications and variations which fall within the scope of the invention as defined by the following claims:

I claim:

1. An adapter for use with an ostomy device of the type including means having an adhesive coated body side for attaching a collection pouch to the body, the adapter comprising a member having a substantially convex surface and a layer of adhesive which overlaps the edge of said member, said member being situated between said adhesive layer and said attaching means with said convex surface adjacent said adhesive layer exposing a substantial portion of said adhesive layer, at least a part of said exposed adhesive layer portion directly contacting said body side of said attaching means.

2. The adapter of claim 1 wherein said member has a substantially annular configuration with a given outer diameter said adhesive layer has a substantially annular configuration with an outer diameter larger than said given outer diameter.

3. The adapter of claim 2 wherein said exposed portion of said adhesive layer is substantially annular.

4. The adapter of claim 1 wherein said member has a central opening with a given diameter and said adhesive layer has a central opening with a diameter smaller than said given diameter.

5. The adapter of claim 4 wherein said exposed portion of said adhesive layer is substantially annular.

6. The adapter of claim 1 wherein said adhesive layer is larger than and overlaps the outer edge of said member.

7. The adapter of claim 1 wherein said adhesive layer has a smaller inner diameter than said member and overlaps the inner edge of said member.

8. The adapter of claim 1 further comprising a plastic shield covering said adhesive layer.

9. The adapter of claim 8 wherein said plastic shield has a contour substantially similar to the contour of said adhesive.

10. The adapter of claim 9 wherein said plastic shield has a substantially wrinkle-free surface.

11. The adapter of claim 1 wherein the attaching means comprises connecting means for detachably mounting a pouch.

12. The adapter of claim 11 wherein said connecting means comprises a relatively rigid coupling ring having a given inner diameter and wherein the outer dimension of said member is smaller than said given inner diameter.

13. The adapter of claim 12 wherein said connecting means comprises a relatively rigid coupling ring defining a circular area on the attaching means with which said member is adapted to align.

14. An adapter for use with an ostomy device of the type including means having an adhesively coated body side for attaching a collection pouch to the body, the adapter comprising a substantially annular member with a substantially convex surface and a substantially annular adhesive wafer, said wafer having a larger diameter than said member and overlapping the outer edge thereof to expose a portion of said wafer, said member being situated between said adhesive wafer and said attaching means with said convex surface adjacent said wafer and said exposed wafer portion contacting said adhesively coated body side of said attaching means such that said body side of said attaching means assumes said substantially convex contour of said annular member surface and a substantially uninterrupted layer of adhesive is formed for attachment of the pouch to the body.

15. The adapter of claim 14 wherein said member has a central opening with a given diameter and said adhesive layer has a central opening with a diameter smaller than said given diameter.

16. The adapter of claim 14 wherein said exposed portion of said adhesive layer is substantially annular.

17. The adapter of claim 15 further comprising an additional exposed portion of said adhesive layer along the rim of said central opening of said member.

18. The adapter of claim 14 further comprising a plastic shield covering said adhesive layer.

19. The adapter of claim 18 wherein said plastic shield has a contour substantially similar to the contour of said adhesive layer.

20. The adapter of claim 19 wherein said plastic shield has a substantially wrinkle-free surface.

21. The adapter of claim 14 wherein the attaching means comprises connecting means for detachably mounting a pouch.

22. The adapter of claim 21 wherein said connecting means comprises a relatively rigid coupling ring having a given inner diameter and wherein the outer diameter of said member is smaller than said given inner diameter.

23. The adapter of claim 21 wherein said connecting means comprises a relatively rigid coupling ring defining a circular area on the attaching means with which said member is adapted to align.

24. An adapter for use with an ostomy device of the type including means having an adhesive coated body side for attaching a collection pouch to the body, the adapter comprising a member having a substantially convex surface and layer of adhesive which overlaps the edge of said member, said member being situated between said adhesive layer and said attaching means with said convex surface adjacent said adhesive layer exposing a portion of said adhesive layer, at least a part of said exposed adhesive layer portion contacting said body side of said attaching means, wherein said member has a central opening with a given diameter and said adhesive layer has a central opening with a diameter smaller than said given diameter.

25. The adapter of claim 24 wherein said exposed portion of said adhesive layer is substantially annular.

* * * * *